United States Patent
Bhadra et al.

(10) Patent No.: US 12,318,614 B2
(45) Date of Patent: Jun. 3, 2025

(54) INTRAVERTEBRAL DIRECT CURRENT BLOCK OF SPINAL TRANSMISSION OF NEURAL SIGNALS

(71) Applicant: Case Western Reserve University, Cleveland, OH (US)

(72) Inventors: Narendra Bhadra, Cleveland, OH (US); Tina L. Vrabec, Cleveland, OH (US); Niloy Bhadra, Cleveland, OH (US); Kevin L. Kilgore, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 17/278,843

(22) PCT Filed: Sep. 27, 2019

(86) PCT No.: PCT/US2019/053410
§ 371 (c)(1),
(2) Date: Mar. 23, 2021

(87) PCT Pub. No.: WO2020/069286
PCT Pub. Date: Apr. 2, 2020

(65) Prior Publication Data
US 2022/0032060 A1     Feb. 3, 2022

Related U.S. Application Data

(60) Provisional application No. 62/737,947, filed on Sep. 28, 2018.

(51) Int. Cl.
*A61N 1/36* (2006.01)
*A61N 1/05* (2006.01)
(Continued)

(52) U.S. Cl.
CPC ....... *A61N 1/36071* (2013.01); *A61N 1/0551* (2013.01); *A61N 1/20* (2013.01); *A61N 1/36139* (2013.01); *A61N 1/37247* (2013.01)

(58) Field of Classification Search
CPC .... A61N 1/36071; A61N 1/0551; A61N 1/20; A61N 1/36139; A61N 1/37247
See application file for complete search history.

(56) References Cited

U.S. PATENT DOCUMENTS

2007/0142874 A1   6/2007  John
2011/0160798 A1   6/2011  Ackermann, Jr. et al.
(Continued)

FOREIGN PATENT DOCUMENTS

WO   2009/061813 A1   5/2009
WO   2011050255 A2    4/2011
WO   2017/062272 A1   4/2017

OTHER PUBLICATIONS

Ackermann Jr, D. Michael, et al. "Separated interface nerve electrode prevents direct current induced nerve damage." Journal of neuroscience methods 201.1 (2011): 173-176.
(Continued)

*Primary Examiner* — Joseph M Dietrich
(74) *Attorney, Agent, or Firm* — Tarolli, Sundheim, Covell & Tummino LLP

(57) ABSTRACT

The present disclose relates to intravertebral electrical block of spinal transmission of neural signals (at least a portion of sensory signals from the peripheral nervous system and/or at
(Continued)

least a portion of motor signals to the peripheral nervous system). At least one intravertebral electrode can be located at a level of a spinal cord of a subject. At least one waveform generator can be coupled to the at least one intravertebral electrode and configured to generate an electrical signal that is sent to the at least one intravertebral electrode for application to the level of the spinal cord of the subject.

18 Claims, 5 Drawing Sheets

(51) Int. Cl.
*A61N 1/20* (2006.01)
*A61N 1/372* (2006.01)

(56) References Cited

U.S. PATENT DOCUMENTS

| | | | |
|---|---|---|---|
| 2013/0281890 A1 | 10/2013 | Mishelevich | |
| 2015/0005680 A1 | 1/2015 | Lipani | |
| 2017/0050024 A1* | 2/2017 | Bhadra | ............. A61N 1/36071 |
| 2018/0256886 A1 | 9/2018 | Bhadra et al. | |

OTHER PUBLICATIONS

Benyamin, Ramsin, Ricardo Vallejo, and David L. Cedeno. "Spinal cord stimulation." Essentials of Interventional Techniques in Managing Chronic Pain. Springer, Cham, 2018. 659-670.
Bhadra, Niloy, and Kevin L. Kilgore. "Direct current electrical conduction block of peripheral nerve." IEEE Transactions on Neural Systems and Rehabilitation Engineering 12.3 (2004): 313-324.
Chakravarthy, Krishnan, et al. "Spinal cord stimulation for treating chronic pain: reviewing preclinical and clinical data on paresthesia-free high-frequency therapy." Neuromodulation: Technology at the Neural Interface 21.1 (2018): 10-18.
Vrabec, Tina, et al. "Characterization of high capacitance electrodes for the application of direct current electrical nerve block." Medical & biological engineering & computing 54.1 (2016): 191-203.
Vrabec, Tina. Direct current block of peripheral nerve: electrode and waveform development. Case Western Reserve University, 2016.
PCT International Search Report for corresponding International Application Serial No. PCT/US2019/00253410, mailed Jun. 12, 2019, pp. 1-4.
Australian Search Report for Corresponding Application Serial No. 2019351023, Dated Nov. 15, 2022, pp. 1-5.
Australian Examination Report No. 1 for corresponding application No. 2023203034, Applicant name: Case Western Reserve University, mailing date Sep. 23, 2024, 5 pages.

* cited by examiner

INTRAVERTEBRAL DIRECT CURRENT BLOCK OF SPINAL TRANSMISSION OF NEURAL SIGNALS

RELATED APPLICATIONS

This application claims priority to U.S. Provisional Application Ser. No. 62/737,947, filed Sep. 28, 2018, entitled "EPIDURAL ELECTRICAL BLOCK OF SPINAL TRANSMISSION OF PERIPHERAL SENSORY SIGNALS". The entirety of this provisional application is hereby incorporated by reference for all purposes.

GOVERNMENT SUPPORT

This invention was made with government support under R01-NS-074149 and R01-NS-089530 awarded by the National Institutes of Health, National Institute of Neurological Disease and Stroke (NIH NINDS). The government has certain rights in this invention.

TECHNICAL FIELD

The present disclosure relates generally to electrical block of transmission of neural signals and, more specifically, to intravertebral direct current (DC) block of spinal transmission of neural signals.

BACKGROUND

Many patients suffer from chronic pain. The chronic pain may be from a wide range of conditions, including chronic back pain, amputated stump pain, neck pain, complex regional pain syndrome, and the like. Many of these patients can benefit from spinal cord stimulation (SCS), which delivers electrical pulses epidurally (or intravertebrally) to modify or mask signals associated with chronic pain before they reach the brain. Some SCS devices use a low frequency (e.g., 50 Hz) current to replace the pain sensation with paresthesia, a mild tingling feeling. Other SCS devices use high frequency (e.g., greater than kilohertz) or burst pulses to mask the pain with no paresthesia, but the high frequency or burst pulses are only shown to be effective for a subset of patients. However, the transmission of peripheral signals into or through the spinal cord is not prevented (or "blocked") by these methods.

SUMMARY

The present disclosure relates to intravertebral direct current (DC) block of spinal transmission of neural signals (at least a portion of peripherally induced sensory signals and/or at least a portion of motor signals in one or more spinal tracts).

In an aspect, the present disclosure can include a system that can provide intravertebral DC block of spinal transmission of neural signals. The system can include at least one intravertebral electrode configured to be located at a level of a spinal cord of a subject. The system can also include at least one waveform generator, coupled to the at least one intravertebral electrode, configured to generate an electrical signal (e.g., including a DC waveform or a charge balanced polarization current (CBPC) waveform) that is sent to the at least one intravertebral electrode for application to the level of the spinal cord of the subject. The electrical signal can be configured to block conduction of neural signals, including at least one peripherally induced spinal sensory signal and/or at least one motor signal in one or more spinal tracts.

In another aspect, the present disclosure can include a method for providing intravertebral DC block of spinal transmission of neural signals. The method can be performed by at least one intravertebral electrode located at a level of a spinal cord of a subject. The method can include receiving an electrical signal (e.g., including a DC waveform or a CBPC waveform) configured to block conduction of neural signals, such as at least one peripherally induced spinal sensory signal and/or at least one motor signal in one or more spinal tract; and delivering the electrical signal to the level of the spinal cord. The conduction of neural signals is at least partially blocked by the electrical signal.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
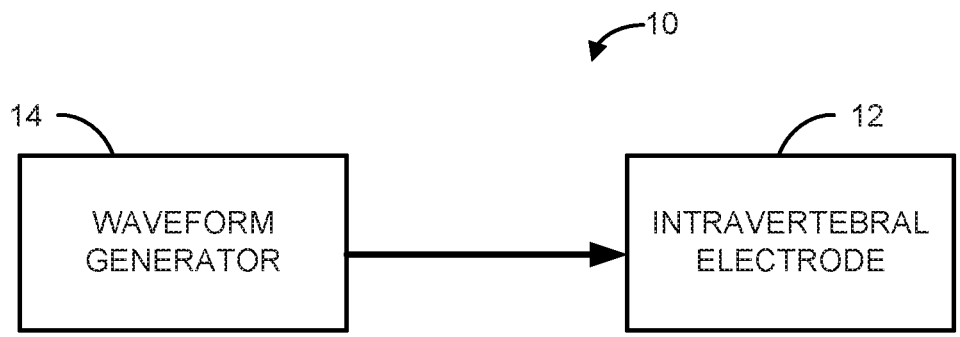
FIG. 1 is a schematic diagram showing an example of a system that can perform intravertebral direct current (DC) block of spinal transmission of neural signals in accordance with an aspect of the present disclosure.

Unless otherwise defined, all technical terms used herein have the same meaning as commonly understood by one of ordinary skill in the art to which the present disclosure pertains.

As used herein, the singular forms "a," "an" and "the" can also include the plural forms, unless the context clearly indicates otherwise.

As used herein, the terms "comprises" and/or "comprising," can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the terms "first," "second," etc. should not limit the elements being described by these terms. These terms are only used to distinguish one element from another.

Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "electrical block" can refer to the attenuation of conduction in neural tissue due to a change in the electric field caused by application of an electrical signal (e.g., a DC waveform) to the neural tissue. Attenuating conduction can refer to extinguishing 100% or less (e.g., 90%, 80%, 70%, 60%, 50%, or the like) of the action potentials traveling through the target neural tissue. In one example, when nerve conduction is attenuated, one or more target nerves within the neural tissue will have an increased activation threshold and thereby make the one or more target nerves more difficult to excite. In another example, the conduction velocity within the one or more target nerves can be decreased when nerve conduction is attenuated.

As used herein, the term "intravertebral" can refer to being inside one or more vertebra. For example, "epidural" is a specific case of "intravertebral", which can be on or within the dura mater of a patient's spinal cord. Another specific case of "intravertebral" is "intraspinal", which can be within the dura or spinal cord (e.g., within the spinal canal).

As used herein, the term "spinal block" can refer to an electrical block of spinal transmission of one or more neural signals (afferent and/or efferent) applied intravertebrally. For example, the spinal block can be of one or more afferent signals (e.g., peripherally induced spinal sensory signals) and/or one or more efferent signals (e.g., motor signals in one or more spinal tracts).

As used herein, the term "partial" spinal block can refer to an electrical block of spinal transmission of a portion of the neural signals (e.g., a portion of afferent signals and/or a portion of efferent signals). As an example, a partial spinal block can be of less than all afferent signals at a certain region (e.g., peripherally induced spinal sensory signals) and/or less than all efferent signals at the certain region (e.g., motor signals in one or more spinal tracts).

As used herein, the term "electrical signal" can refer to a time-varying observable change in a quantifiable entity, such as voltage or current. In some instances, the electrical signal can be a direct current (DC) waveform and/or a charge balanced polarization current (CBPC) waveform (a modified DC waveform).

Application of a DC or a CBPC to cause a spinal block can be referred to as a "DC block" or "DC nerve conduction block". The DC block can be fast acting, reversible, onset free, and easy to modulate.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

As used herein, the term "spinal cord" can refer to the long, thin, tubular structure that can transmit neural signals. As used herein, the term "spine" can refer to the vertebrae that protect the spinal cord. However, the terms "spinal cord" and "spine" may be used interchangeably to refer to ether the spinal cord or the spine individually and/or a combination of the spinal cord and the spine.

II. Overview

Traditional spinal cord stimulation (SCS) involves the application of electrical pulses (e.g., at a low frequency, like 50 Hertz, or at a high frequency, greater than kiloHertz) to a portion of the spinal column through an intravertebral electrode. However, the application of low or high frequency does not directly block transmission of signals within the spinal cord, but rather relies on indirect means of blocking pain signals. The lack of efficacy of traditional SCS may be due to the electrical pulses not being able to block the transmission of peripheral signals into or through the spinal cord. One waveform that has been shown to provide a complete conduction block in the peripheral nervous system is DC nerve conduction block (due to the application of a direct current (DC) waveform and/or a charge balanced polarization current (CBPC) waveform).

DC nerve conduction block is attractive for many applications because it is fast acting, reversible, onset free, and easy to modulate. However, DC nerve conduction block has not been used clinically due its high likelihood of causing tissue damage. When DC nerve conduction block is applied to neural tissue via traditional electrodes (e.g., through traditional intravertebral electrodes used for SCS) for a prolonged period of time, Faradaic reactions like hydrogen evolution, oxygen evolution, chlorine evolution, or the like, can occur and cause damage to the interface between the tissue and the electrode applying the DC nerve conduction block. New electrode designs (e.g., utilizing a saline interface and/or high capacitance electrode materials and designs) can circumvent this tissue damage. The new electrode designs can be used to create new intravertebral electrodes that can deliver a DC waveform or a CBPC waveform for SCS that actually provides a block of the transmission of at least a portion of peripherally induced sensory signals and/or at least a portion of motor signals in one or more spinal tracts.

III. Systems

An aspect of the present disclosure can include a system 10 (FIG. 1) that can perform intravertebral direct current (DC) block of spinal transmission of neural signals. In some instances, the DC block can be provided due to the application of a DC waveform (configured for the specific application) to a portion of the spinal cord. In other instances, the DC block can be provided due to the application of a charge balanced polarization current (CBPC) waveform (configured for the specific application). The system 10 is superior to traditional spinal cord stimulation (SCS) blocking techniques at least because the DC block stops (or, in other words, blocks) the transmission of at least a portion of neural signals in a patient's spine, such as at least a portion of peripherally induced sensory signals and/or at least a portion of motor signals in one or more spinal tracts.

The system 10 includes one or more intravertebral electrodes (one shown in FIG. 1 as intravertebral electrode 12) and one or more waveform generator 14 (one shown in FIG. 1 as waveform generator 14). The intravertebral electrode(s) 12 can be coupled to the waveform generator(s) 14 for signal transmission. As an example, the coupling can be a wired coupling to transmit a signal at least from the waveform generator(s) 14 to the intravertebral electrode(s) 12.

The intravertebral electrode(s) 12 can be configured to be located at one or more levels of the patient's spinal cord. For example, one intravertebral electrode 12 can be located at a single level of the patient's spinal cord. As another example, two intravertebral electrodes can be located at two separate levels of the patient's spinal cord. As a further example, two intravertebral electrodes can both be located at a single level of the patient's spinal cord. The levels of the patient's spinal cord can be one or more sacral levels (e.g., selected from S1-S5), one or more thoracic levels (e.g., selected from T1-T12), and/or one or more lumbar levels (e.g., selected from L1-L5).

The electrode(s) 12 can be intravertebral electrodes shaped like a traditional SCS electrode that is configured for implantation to a level of a patient's spinal cord (e.g., through a sacral foramen, a surgical fenestration in a lumbar lamina, or the like). However, in order to receive the benefits of DC block (e.g., a conduction block that is fast acting, reversible, onset free, easily modulated, etc.) without causing tissue damage to the patient's spinal cord, the electrode(s) 12 must be design to avoid Faradaic reactions, like hydrogen evolution, oxygen evolution, chlorine evolution, or the like. For example, the electrode(s) 12 can utilize a saline interface. As another example, the electrode(s) 12 can utilize high capacitance electrode materials. Specific examples of electrodes that can be used as the electrode(s) 12 include a separated interface nerve electrode (SINE), a carbon coated platinum electrode, a woven cloth carbon electrode, a carbon slurry electrode, or the like (e.g., designed as described in at least one of U.S. Pat. Nos. 9,008,800, 9,496,621, WO 2019/133783, WO 2019/133784, U.S. Pat. No. 9,387,322, or 10,195,434, which are incorporated herein by reference).

The waveform generator(s) 14 can be configured or programmed to generate the electrical signal that is configured to block at least a portion of conduction in the spinal cord. For example, the electrical signal can be configured with an amplitude sufficient to cause the DC block in at least a portion of the spinal cord at the level of the spinal cord. The electrical signal can include a DC waveform, like a DC or a CBPC, configured to block the at least the portion of the conduction at the level of the spinal cord when applied to the level of the spinal cord by the electrode(s) 12. For example, the electrical signal can be configured to block conduction of configured to block conduction of peripherally induced spinal sensory signals and/or motor signals in one or more spinal tracts.

Accordingly, the waveform generator 14 can be any device configured or programmed to generate the specified electrical signal. One example of a waveform generator 14 is a battery-powered, portable generator. Another example of a waveform generator 14 is an implantable generator (IPG). It will be appreciated that the waveform generator 14 can include additional components to selectively configure the current waveform, such as an amplitude modulator (not shown). In some instances, the generated DC waveform can have an anodic polarity or a cathodic polarity, and an amplitude sufficient to cause the DC block. As an example, the waveform generator 14 can be configured or programmed to generate a DC waveform having monophasic waveform or a biphasic waveform, with one phase cathodic and one anodic. As another example, the waveform generator 14 can be configured or programmed to generate a CBPC waveform.

Figure 2:
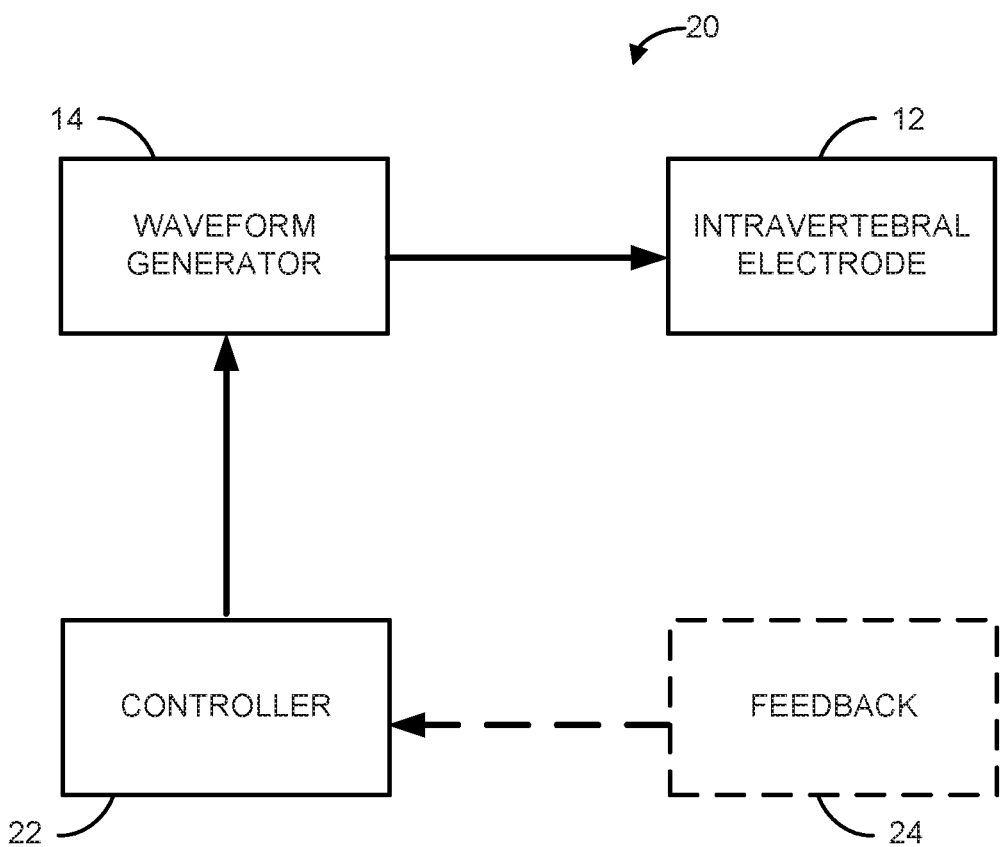
FIG. 2 shows an example of the system of claim 1 with the waveform generator receiving input from a controller.

As shown in FIG. 2, the waveform generator(s) 14 can be coupled to one or more controllers (shown as a single controller 22 in FIG. 2). The controller(s) 22 can be configured to set one or more parameters of the electrical signal delivered by the waveform generator 14. In some instances, the controller(s) 22 can be programmed with set values for the one or more parameters. In other instances, the controller(s) 22 can alter a value of the one or more parameters based on feedback 24. For example, the feedback 24 can be a user input (in this example, the controller 22 can have safety concerns programmed therein to prevent the one or more parameters to be adjusted to an unsafe or ineffective level. As another example, the feedback 24 can be from a sensor within the subject's body either before delivery of the DC block or after delivery of the DC block.

IV. Methods

Figure 3:
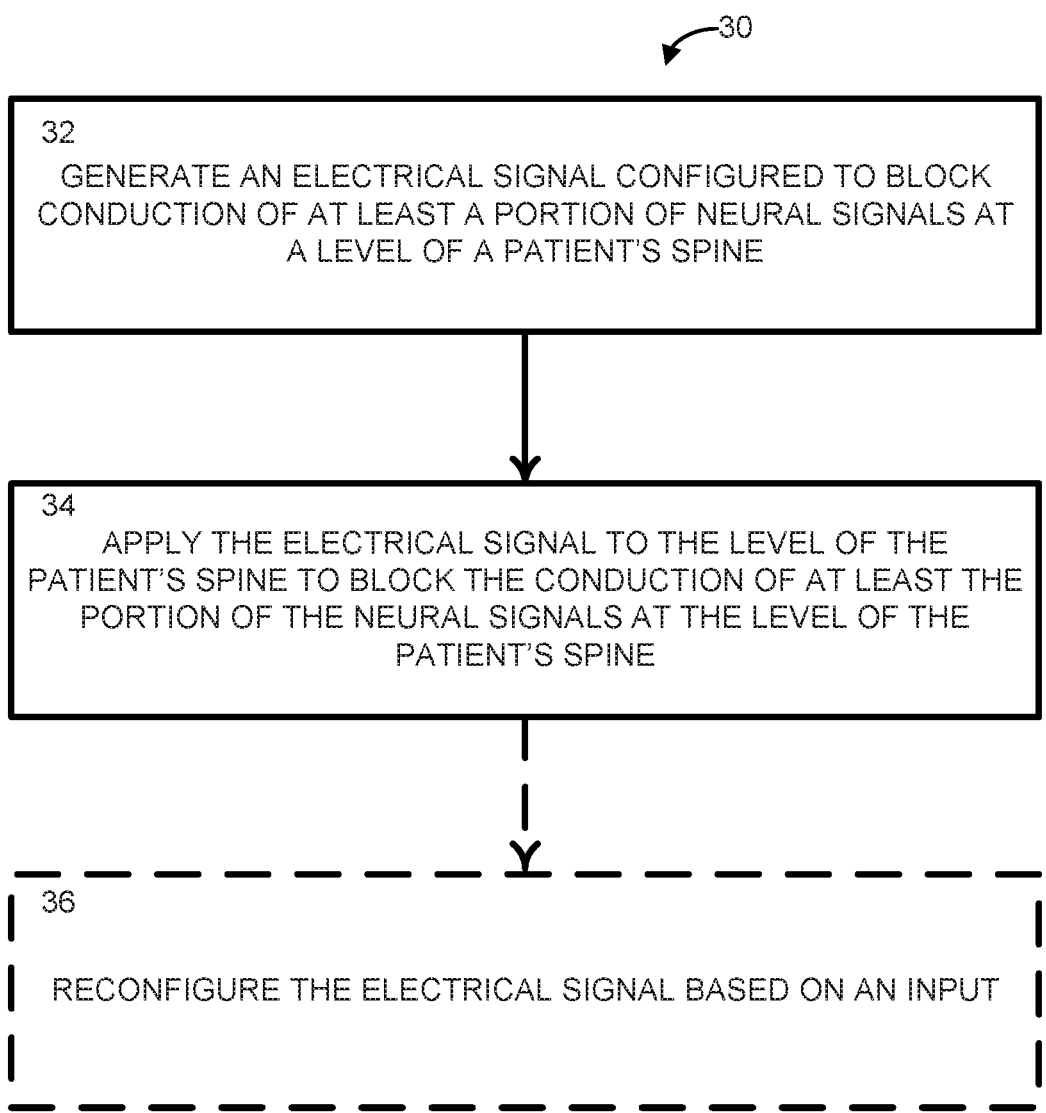
FIGS. 3 and 4 are process flow diagrams illustrating methods for performing intravertebral direct current (DC) block of spinal transmission of neural signals according to another aspect of the present disclosure.
Figure 4:
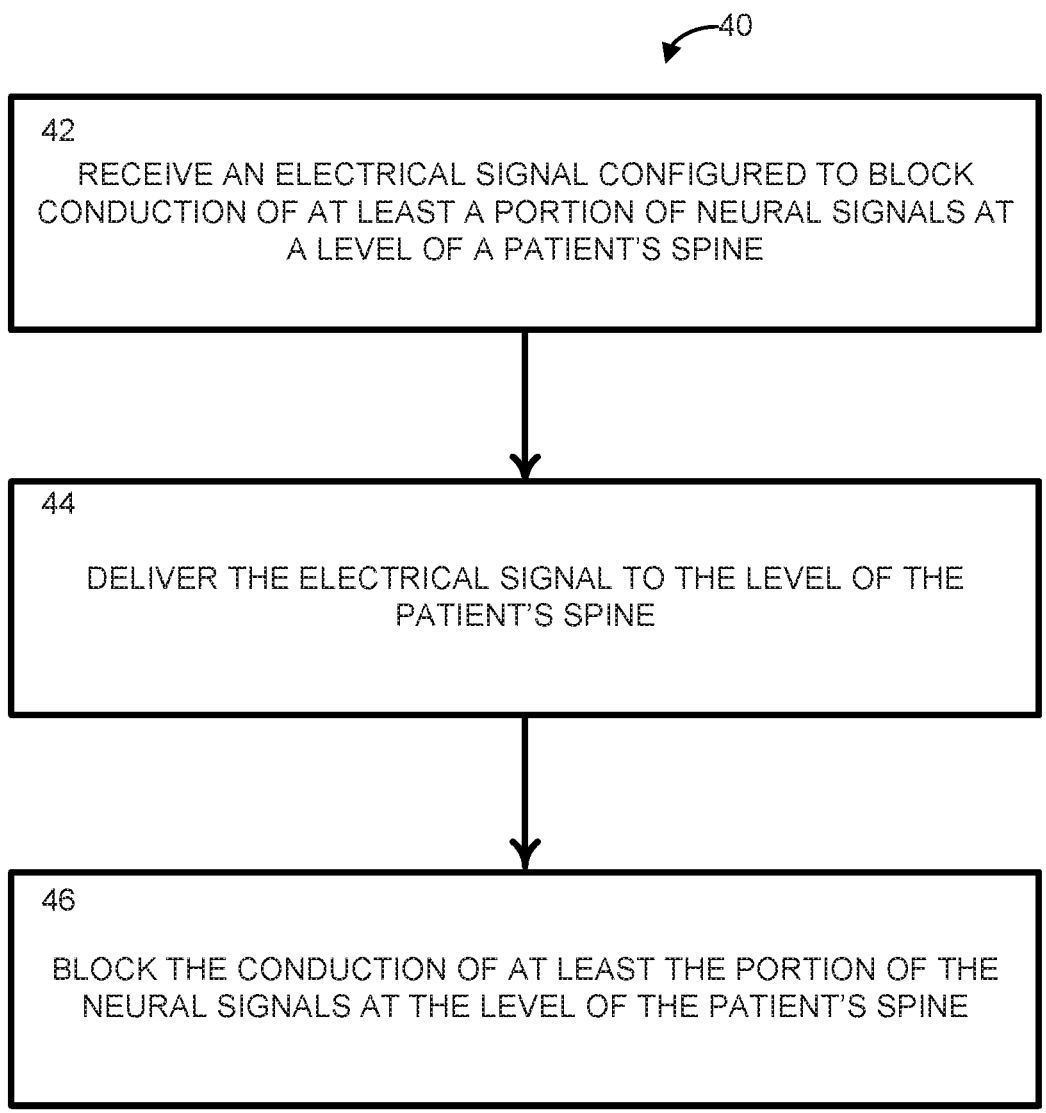

Another aspect of the present disclosure can include methods 30 and 40 for performing intravertebral direct current (DC) block of spinal transmission of neural signals, as shown in FIGS. 3 and 4. The methods 30 and 40 can be executed using the systems 10 or 20 shown in FIGS. 1 and 2, using the intravertebral electrode(s) 12 designed to avoid Faradaic reactions, like hydrogen evolution, oxygen evolution, chlorine evolution, or the like. For example, the electrode(s) 12 can utilize a saline interface. As another example, the electrode(s) 12 can utilize high capacitance electrode materials. Specific examples of electrodes that can be used as the electrode(s) 12 include a separated interface nerve electrode (SINE), a carbon coated platinum electrode, a woven cloth carbon electrode, a carbon slurry electrode, or the like.

For purposes of simplicity, the methods 30 and 40 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 30 and 40.

Referring now to FIG. 3, illustrated is an example of a method 30 for performing intravertebral DC block of spinal transmission of neural signals. At Step 32, an electrical signal can be generated (e.g., by waveform generator 14) that is configured to block conduction of at least a portion of neural signals at a level of a patient's spine. As an example, the electrical signal can be configured with an amplitude sufficient to cause the DC block in at least a portion of the spinal cord at the level of the spinal cord. The electrical signal can include a DC waveform, like a DC or a CBPC, configured to block the at least the portion of the conduction at the level of the spinal cord when applied to the level of the spinal cord. For example, the electrical signal can be configured to block conduction of configured to block conduction of peripherally induced spinal sensory signals and/or motor signals in one or more spinal tracts. The level of the patient's spinal cord can be one or more sacral levels (e.g., selected from S1-S5), one or more thoracic levels (e.g., selected from T1-T12), and/or one or more lumbar levels (e.g., selected from L1-L5).

At Step 34, the electrical signal can be applied (e.g. by intravertebral electrode 12) to the level of the patient's spine to block the conduction of at least the portion of the neural signals at the level of the patient's spine. In order to receive the benefits of DC block (e.g., a conduction block that is fast acting, reversible, onset free, easily modulated, etc.) without causing tissue damage to the patient's spinal cord, the intravertebral electrode must be design to avoid Faradaic reactions, like hydrogen evolution, oxygen evolution, chlorine evolution, or the like. For example, the electrode can utilize a saline interface. As another example, the electrode can utilize high capacitance electrode materials. Specific examples of electrodes that can be used as the electrode(s) 12 include a separated interface nerve electrode (SINE), a carbon coated platinum electrode, a woven cloth carbon electrode, a carbon slurry electrode, or the like. Optionally, at Step 36, the electrical signal can be reconfigured based on an input (e.g., input as feedback 24 to a controller 22, user input and/or sensor input).

Referring now to FIG. 4, illustrated is another example of a method 40 for performing intravertebral DC block of spinal transmission of neural signals. At Step 42, an electrical signal (e.g., a DC waveform or a CBPC waveform) can be received (e.g., by an intravertebral electrode 12) that is configured to block conduction of at least a portion of neural signals at a level of a patient's spine (e.g., where the intravertebral electrode 12 is implanted). At Step 44, the electrical signal can be delivered (e.g., by the intravertebral electrode 12) to the level of the patient's spine. At Step 46, the conduction of at least the portion of the neural signals at the level of the patient's spine can be blocked (or stopped, in other words) by the electrical signal. The electrical signal can be configured specifically to block the conduction of at least the portion of the neural signals.

V. Examples

The following example describes procedure and results of experimental application of DC via intravertebral electrodes to block transmission of peripheral sensory signals into the spinal cord in anesthetized rodent preparations The following example is for the purpose of illustration only is not intended to limit the scope of the appended claims.

Methods

Figure 5:
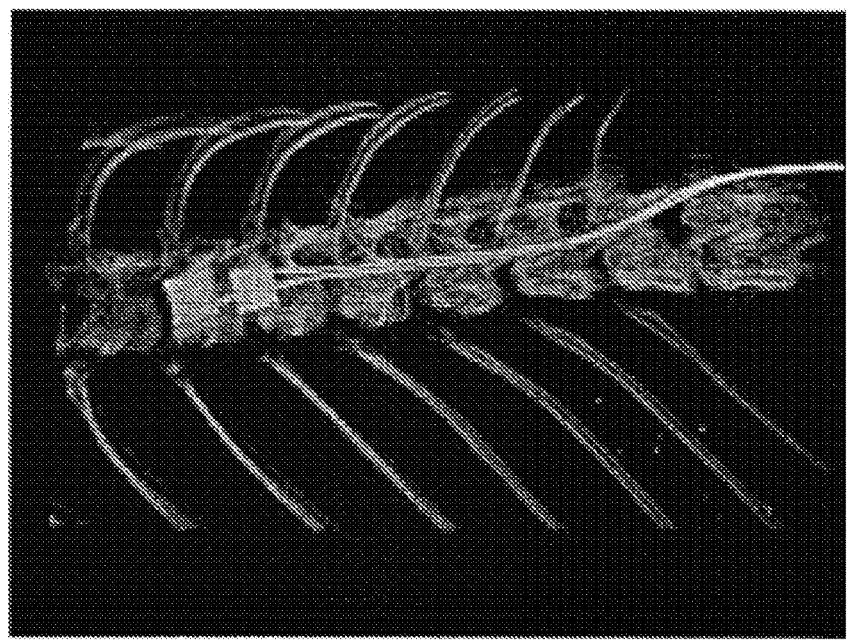
FIG. 5 shows a computed tomography (CT) scan image of an implanted spinal specimen from a test animal showing a bipolar electrode at a 8th thoracic vertebra level for intravertebral recording of evoked spinal potentials.

Bipolar recording electrodes (FIG. 5) or tripolar recording electrodes were placed intravertebrally over the lower thoracic spinal segments through a lumbar laminectomy in anesthetized rats for recording peripherally induced sensory signals.

Peripheral sensory signals were induced with electrical pulses (1 ms width, 1-2 mA amplitude) at 1 Hz with subcutaneous needle electrodes in the fourth web of one hind limb (S1 dermatome segment).

Figure 6:
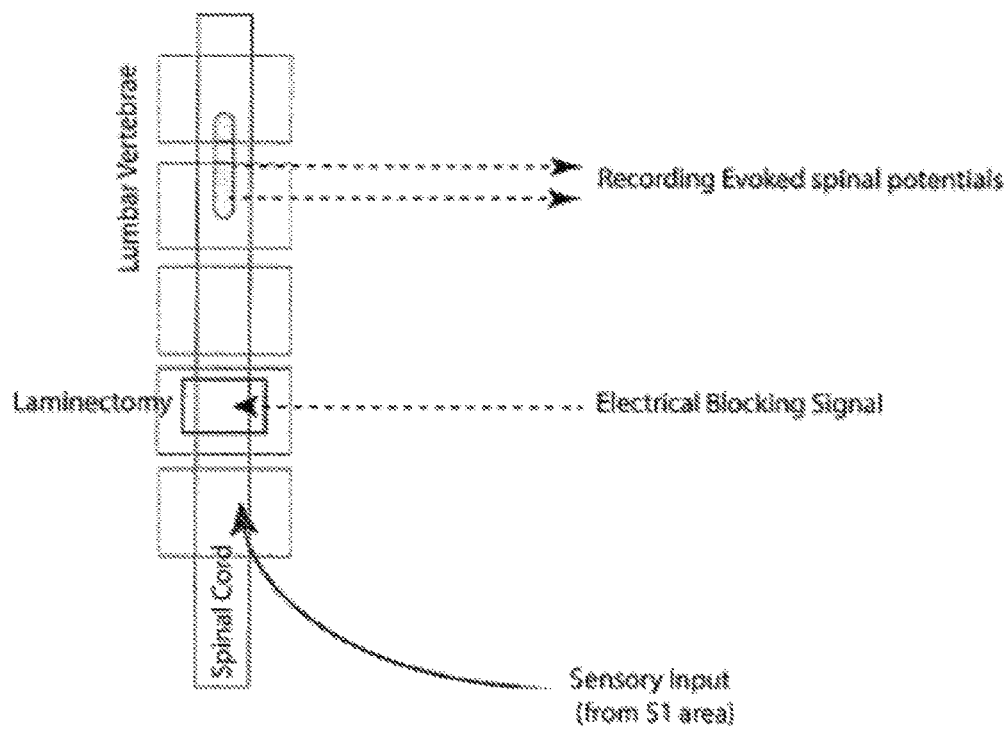
FIG. 6 shows a schematic of in vivo experimental preparation in anesthetized rodents.

Electrical blocking signals were applied intravertebrally at the lowest thoracic or highest lumbar vertebral level with electrodes placed at a surgical laminectomy (FIG. 6).

Spinal Somato-Sensory Evoked potentials (SSEP) were recorded during peripheral stimulation, with and without blocking signals applied intravertebrally to the spinal cord.

Results

Figure 7:
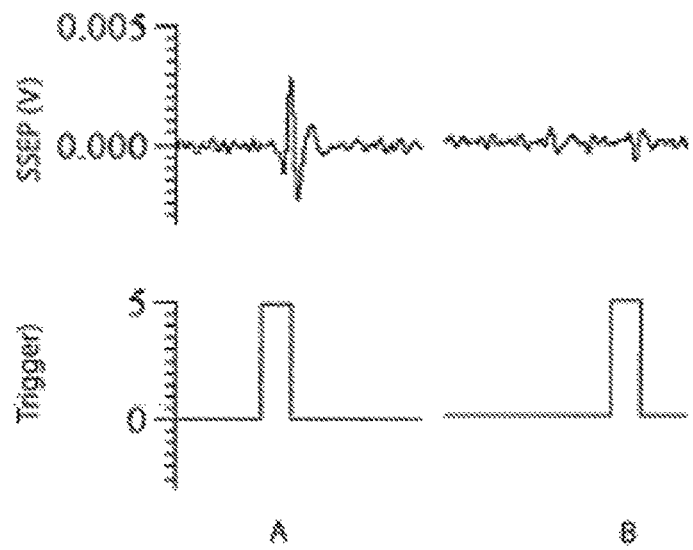
FIG. 7 shows an example of Somato-Sensory Evoked Potentials SSEP) recorded by a rodent spinal preparation, (A) before and (B) after application of an electrical DC block signal.

An example of Somato-Sensory Evoked Potentials (SSEP) recorded from a rodent spinal preparation, (A) before and (B) after application of an electrical blocking signal is shown in FIG. 7. Electrical block of transmission of peripherally induced sensory signals was demonstrated by diminution or absence of SSEP recorded (as shown in (B) compared to (A)). Similar results were seen in the following preparations: charge balanced polarization current (CBPC) waveform with a Carbon coated Platinum electrode, CBPC waveform with Separated Interface Nerve Electrode (SINE), CBPC waveform with a woven cloth Carbon electrode, and direct current (DC) waveform with a Carbon Slurry electrode.

Other Uses of this Procedure

Figure 8:
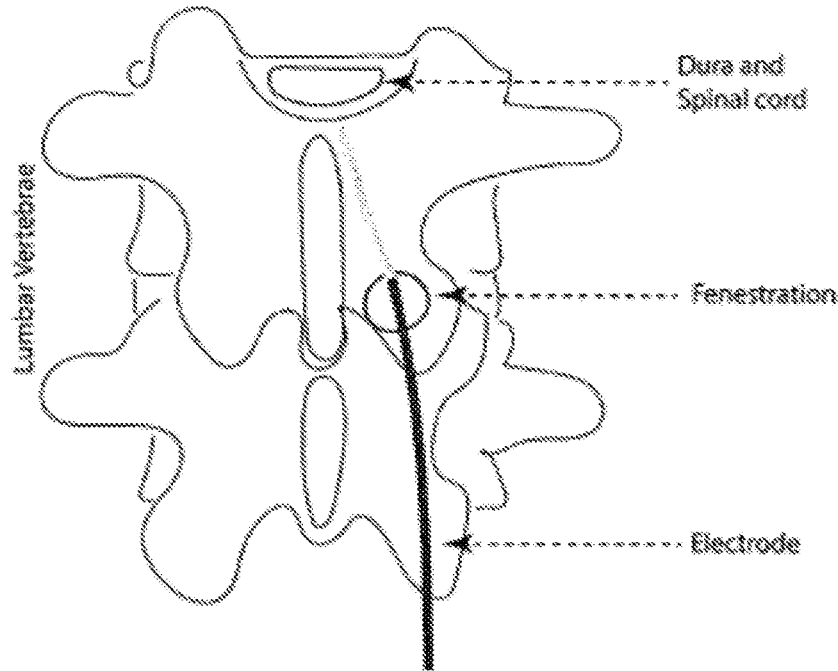
FIG. 8 shows an example implantation of an intravertebral electrode that can perform intravertebral DC block of spinal transmission of neural signals.

Suppression and recovery of SSEP recorded from rostral locations in the spinal cord of distal sensory stimulation during intravertebral DC blocking signals shows that this procedure can be used to provide temporary conduction block at the spinal level (e.g., for the treatment of pain, such as neuropathic pain). The procedure can be applied to block other spinal locations and spinal pathways for the relief of other neurologically mediated disorders. The blocking scheme can be clinically implemented with electrodes placed intravertebrally through a sacral foramen or through a fenestration (or window) on a lamina of a lumbar vertebrae (FIG. 8).

From the above description, those skilled in the art will perceive improvements, changes and modifications. Such improvements, changes and modifications are within the skill of one in the art and are intended to be covered by the appended claims.

The following is claimed:

1. A method comprising:
    receiving, by at least one intravertebral electrode surgically implanted into dura at a level of a spinal cord of a subject and by at least one other intravertebral electrode surgically implanted into the dura at another level of the spinal cord of the subject, an electrical signal configured to block spinal transmission of at least a portion of peripherally induced sensory signals, wherein the electrical signal comprises a direct current waveform, and wherein the at least one intravertebral electrode and the at least one other intravertebral electrode each comprise a high-capacitance electrode material; and
    delivering, by the at least one intravertebral electrode and the at least one other intravertebral electrode, the electrical signal to the level of the spinal cord and the other level of the spinal cord, respectively, wherein delivery of the electrical signal to the level of the spinal cord and the other level of the spinal cord blocks spinal transmission of at least the portion of the peripherally induced sensory signals in one or more spinal tracts at the level of the spinal cord and the other level of the spinal cord.

2. The method of claim 1, wherein the high-capacitance electrode material comprises carbon.

3. The method of claim 2, wherein the high-capacitance electrode material comprises is a carbon coated platinum electrode, a woven cloth carbon electrode, or a carbon slurry electrode.

4. The method of claim 1, wherein the at least one intravertebral electrode and/or the at least one other intravertebral electrode is a separated interface nerve electrode (SINE).

5. The method of claim 1, wherein the level of the spinal cord is at least one of and the other level of the spinal cord is at least one other of a sacral level of the spine, a thoracic level of the spine, and/or a lumbar level of the spine.

6. The method of claim 1, further comprising inserting the at least one intravertebral electrode and/or the at least one other intravertebral electrode through a sacral foramen, wherein the level of the spinal cord comprises at least a sacral level of the spine.

7. The method of claim 1, further comprising inserting the at least one intravertebral electrode and/or the at least one other intravertebral electrode through a surgical fenestration in a lumbar lamina, wherein the level of the spinal cord comprises at least a lumbar level of the spine.

8. The method of claim 1, further comprising generating, by a waveform generator device coupled to the at least one intravertebral electrode and the at least one other intravertebral electrode, the electrical signal configured to block spinal transmission of at least the portion of peripherally induced sensory signals.

9. The method of claim 8, further comprising receiving, by the waveform generator, an input corresponding to a value of at least one of the one or more parameters.

10. A system comprising:
- at least one intravertebral electrode configured to be surgically implanted into dura at a level of a spinal cord of a subject, wherein the at least one intravertebral electrode comprises a high-capacitance electrode material;
- at least one other intravertebral electrode configured to be surgically implanted into dura at another level of the spinal cord of the subject, wherein the at least one other intravertebral electrode comprises the high-capacitance electrode material; and
- at least one waveform generator, coupled to the at least one intravertebral electrode and the at least one other intravertebral electrode, configured to generate an electrical signal comprising a direct current waveform that is sent to the at least one intravertebral electrode and the at least one other intravertebral electrode for application to the level of the spinal cord of the subject and the other level of the spinal cord of the subject, wherein the electrical signal comprising the direct current waveform is configured to block spinal transmission of at least a portion of peripherally induced sensory signals in one or more spinal tracts at the level of the spinal cord and the other level of the spinal cord.

11. The system of claim 10, wherein the high-capacitance electrode material comprises a separated interface nerve electrode (SINE), a carbon coated platinum electrode, a woven cloth carbon electrode, or a carbon slurry electrode.

12. The system of claim 10, wherein the level of the spinal cord is at least on of and the other level of the spinal cord is at least one other of a sacral level of the spine, a thoracic level of the spine, and/or a lumbar level of the spine.

13. The system of claim 10, wherein the at least one intravertebral electrode and/or the at least one other intravertebral electrode is configured to be inserted through a sacral foramen in the subject's body, wherein the level of the spinal cord comprises at least a sacral level of the spine.

14. The system of claim 10, further comprising a controller, coupled to the waveform generator, configured to set one or more parameters of the electrical signal.

15. The system of claim 14, wherein the controller is configured to set the one or more parameters of the electrical signal based on a feedback signal from a sensor within the subject's body.

16. The system of claim 14, wherein the controller is configured to set the one or more parameters of the electrical signal based on a user input.

17. The method of claim 1, wherein the electrical signal at least partially blocks spinal transmission of the at least the portion of the peripherally induced sensory signals.

18. The system of claim 10, wherein the at least one intravertebral electrode and the at least one other intravertebral electrode are configured to apply the electrical signal comprising the direct current waveform to block spinal transmission of the at least the portion of the peripherally induced sensory signals without causing a Faradaic reaction.

* * * * *